US00PP33519P3

(12) United States Plant Patent
Post

(10) Patent No.: US PP33,519 P3
(45) Date of Patent: Sep. 28, 2021

(54) CHRYSANTHEMUM PLANT NAMED 'DLFEMPR11'

(50) Latin Name: ***Chrysanthemum* X *morifolium***
Varietal Denomination: DLFEMPR11

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/089,720

(22) Filed: Nov. 5, 2020

(65) Prior Publication Data

US 2021/0136985 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./291
CPC ..... *A01H 6/1424* (2018.05)

(58) Field of Classification Search
USPC ..... Plt./291
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFEMPR11', characterized by its upright plant habit; vigorous growth habit and rapid growth rate; dark green-colored leaves; typically grown as a disbud-type; strong upright flowering stems; large decorative-type inflorescences with pale purplish pink-colored ray florets; relative tolerance to high production temperatures; resistance to Fusarium Wilt; and good postproduction longevity.

2 Drawing Sheets

Figure 1:
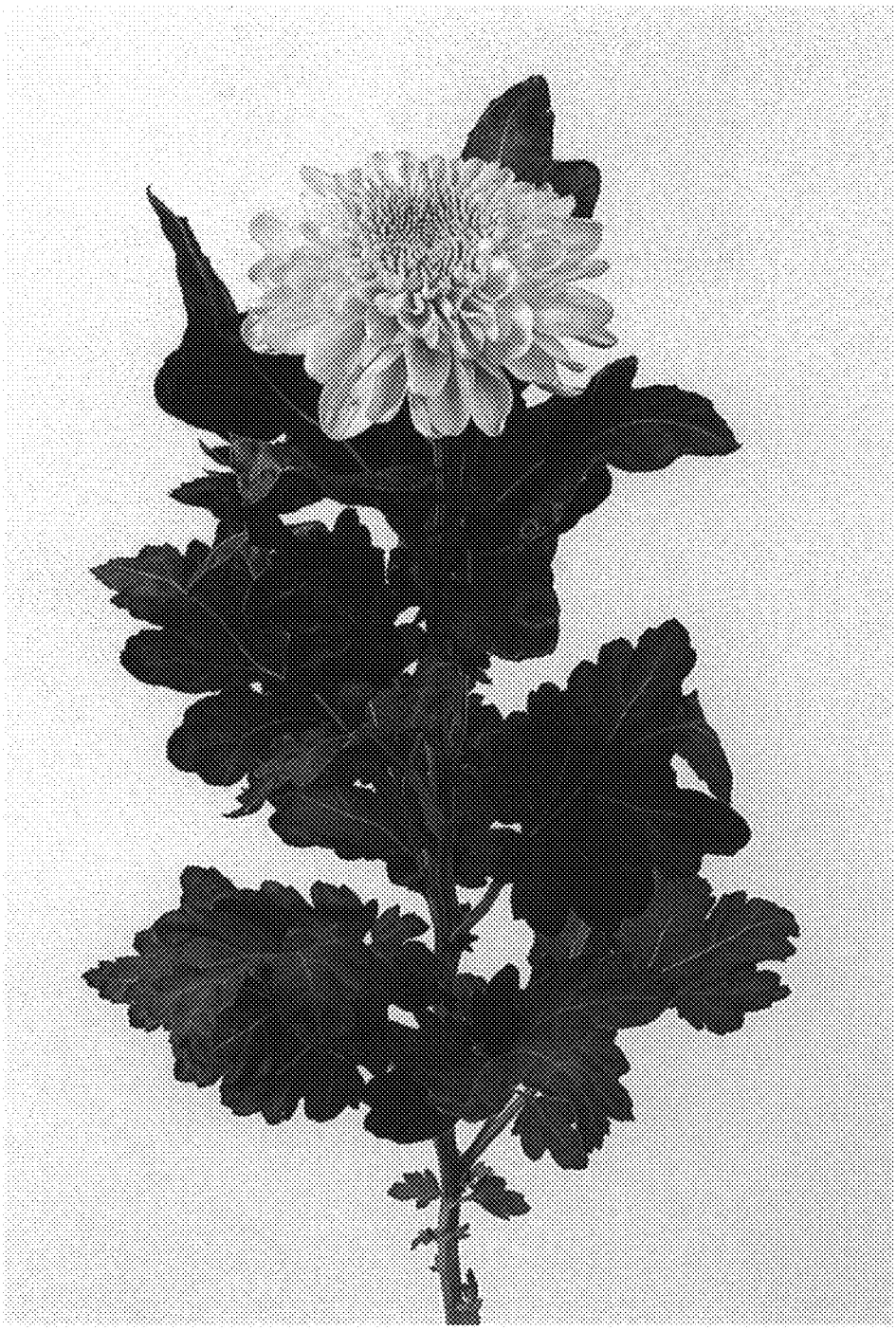
Figure 2:
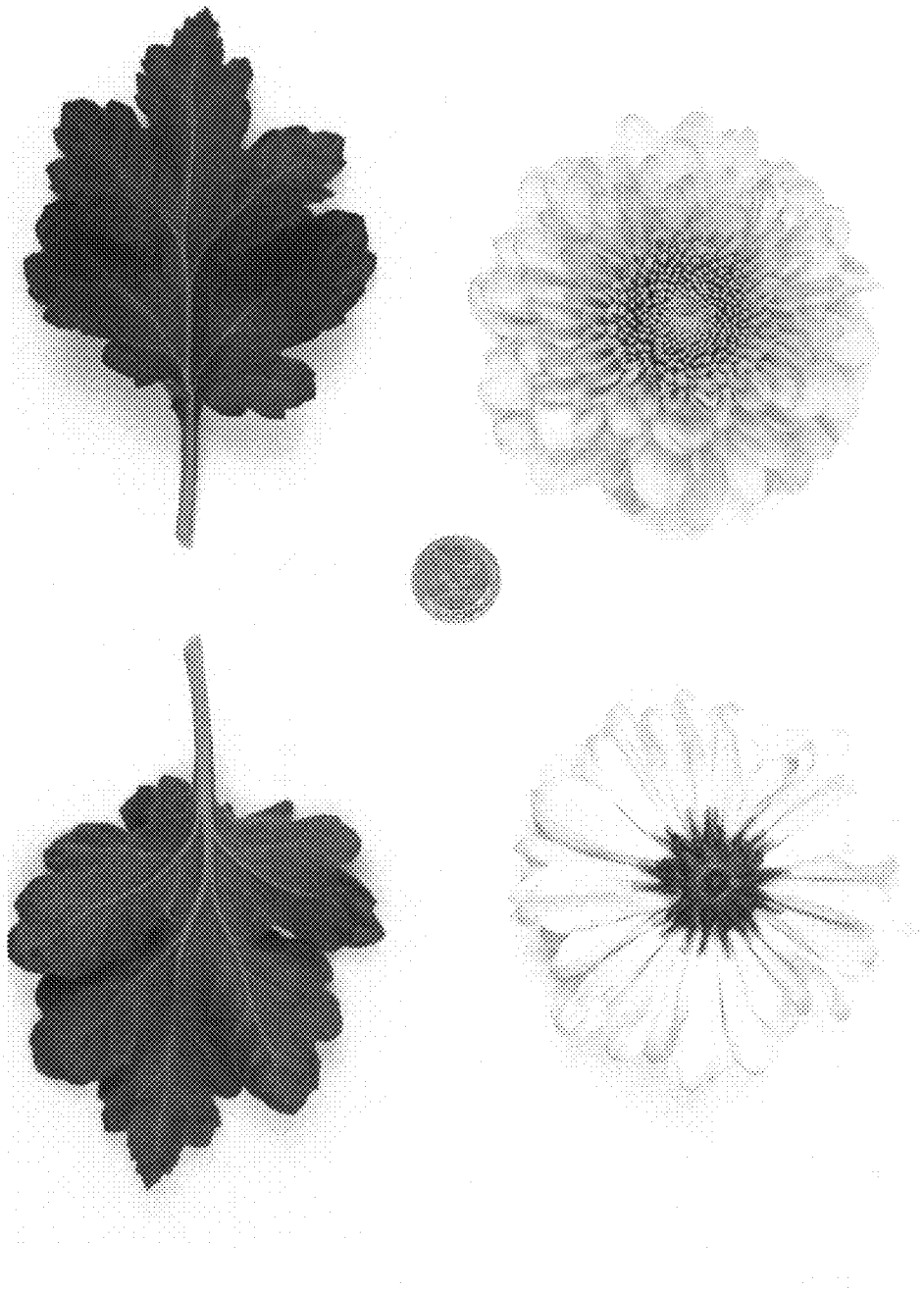

Botanical designation: *Chrysanthemum* X *morifolium*.
Cultivar denomination: 'DLFEMPR11'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFEMPR11'.

The new *Chrysanthemum* plant is a product of a planned breeding program conducted by the Inventor in Maasdijk, The Netherlands. The objective of the breeding program is to create new cut flower *Chrysanthemum* plants with attractive inflorescences.

The new *Chrysanthemum* plant originated from a cross-pollination in February, 2012 of a proprietary selection of *Chrysanthemum* x *morifolium* identified as code number db 33444, not patented, as the female, or seed, parent with a proprietary selection of *Chrysanthemum* x *morifolium* identified as code number db 11181, not patented, as the male, or pollen, parent. The new *Chrysanthemum* plant was discovered and selected as a single flowering plant from within the progeny of the stated cross-pollination in a controlled greenhouse environment in Maasdijk, The Netherlands in December, 2013.

Asexual reproduction of the new *Chrysanthemum* plant by vegetative terminal cuttings since December, 2013 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFEMPR11'. These characteristics in combination distinguish 'DLFEMPR11' as a new and distinct *Chrysanthemum* plant:

1. Upright plant habit.
2. Vigorous growth habit and rapid growth rate.
3. Dark green-colored leaves.
4. Typically disbudded and grown as a single-stem.
5. Strong upright flowering stems.
6. Large decorative-type inflorescences with pale purplish pink-colored ray florets.
7. Relatively tolerant to high production temperatures.
8. Resistant to Fusarium Wilt.
9. Good postproduction longevity.

Plants of the new *Chrysanthemum* differ primarily from plants of the female parent selection in ray floret color as plants of the new *Chrysanthemum* have lighter purplish pink-colored ray florets than plants of the female parent selection. In addition, plants of the new *Chrysanthemum* are more tolerant to high production temperatures than plants of the female parent selection.

Plants of the new *Chrysanthemum* differ primarily from plants of the male parent selection in ray floret color as plants of the new *Chrysanthemum* have pale purplish pink-colored ray florets whereas plants of the male parent selection have white-colored ray florets. In addition, plants of the new *Chrysanthemum* have smaller inflorescences than plants of the male parent selection.

Plants of the new *Chrysanthemum* can be compared to plants of *Chrysanthemum* X *morifolium* 'Delirossano', not patented. In side-by-side comparisons, plants of the new *Chrysanthemum* differ primarily from plants of 'Delirossano' in ray floret color as plants of the new *Chrysanthemum* have pale purplish pink-colored ray florets whereas ray florets of 'Delirossano' are very pale purple in color. In addition, developing ray florets of plants of the new *Chrysanthemum* are yellowish green in color whereas developing ray florets of plants of 'Delirossano' are pink in color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFEMPR11' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFEMPR11'.

Parentage:

*Female, or seed, parent.*—Proprietary selection of *Chrysanthemum* x *morifolium* identified as code number db 33444, not patented.

*Male, or pollen, parent.*—Proprietary selection of *Chrysanthemum* x *morifolium* identified as code number db 11181, not patented.

Propagation:

*Type.*—Terminal vegetative cuttings.

*Time to initiate roots, summer.*—About four days at temperatures about 20° C.

*Time to initiate roots, winter.*—About five days at temperatures about 20° C.

*Time to produce a rooted young plant, summer.*—About twelve days at temperatures about 22° C.

*Time to produce a rooted young plant, winter.*—About 14 days at temperatures about 20° C.

*Root description.*—Fine, fibrous; typically light brown in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous decorative-type cut flower that is typically grown as a single stem disbud-type; upright plant habit; vigorous growth habit and rapid growth rate.

*Plant height, soil level to top of foliar plane.*—About 84.5 cm.

*Plant height, soil level to top of inflorescence plane.*—About 88.1 cm.

*Plant (spray) diameter.*—About 22.6 cm.

*Flowering stem length.*—About 78.4 cm.

*Flowering stem diameter.*—About 7.5 mm.

*Flowering stem internode length.*—About 2.9 cm.

*Flowering stem strength.*—Strong.

*Flowering stem aspect.*—Erect.

*Flowering stem texture and luster.*—Densely pubescent; slightly glossy.

*Flowering stem color, developing.*—Close to 144A to 144B.

*Flowering stem color, developed.*—Close to 144A.

*Leaf description.*—Arrangement: Alternate; simple. Length: About 14.2 cm. Width: About 9.5 cm. Shape: Broadly ovate to broadly oblong. Apex: Abruptly acute. Base: Attenuate. Margin: Palmately lobed, coarsely dentate; sinuses convergent and medium to deep in depth. Texture and luster, upper surface: Moderately pubescent, not rugose; moderately velvety; very slightly glossy. Texture and luster, lower surface: Densely pubescent, prominent venation; slightly velvety; very slightly glossy. Venation pattern: Pinnate, reticulate. Color: Developing leaves, upper surface: Close to between NN137A and 147A. Developing leaves, lower surface: Close to 147B. Fully developed leaves, upper surface: Close to NN137A; venation, close to 147C. Fully developed leaves, lower surface: Close to 147B; venation, close to 147C. Petioles: Length: About 3.1 cm. Diameter: About 3 mm by 4 mm. Strength: Moderately strong. Texture and luster, upper and lower surfaces: Moderately to densely pubescent; slightly glossy. Color, upper surface: Close to 146B; edges, slightly darker than 143A. Color, lower surface: Close to 147C; edges, slightly darker than 143A. Stipules: Quantity and appearance: Two leafy stipules, opposite, at the petiole attachment to the stem. Length: About 1.5 cm. Width: About 1.4 cm. Shape: Broadly obovate. Texture and luster, upper surface: Moderately pubescent, not rugose; moderately velvety; very slightly glossy. Texture and luster, lower surface: Densely pubescent, prominent venation; slightly velvety;

very slightly glossy. Color, upper surface: Close to NN137A. Color, lower surface: Close to 147B.

Inflorescence description:

*Appearance.*—Decorative-type inflorescence form with oblanceolate-shaped ray florets and tubular disc florets; inflorescences borne perpendicular to peduncles and face upright; ray and disc florets develop acropetally on a capitulum.

*Fragrance.*—Faintly fragrant; typical of *Chrysanthemums.*

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a spray-type.

*Postproduction longevity.*—Good postproduction longevity; in an interior environment, inflorescences and foliage will maintain good color and substance for about two weeks; inflorescences persistent.

*Quantity of inflorescences.*—Typically grown as a disbud-type, however, when grown as a spray-type, about nine inflorescences develop per flowering stem.

*Inflorescence size.*—Diameter, grown as a disbud-type: About 10.9 cm. Diameter, grown as a spray-type: About 8.9 cm. Depth (height), grown as a disbud-type: About 7.9 cm. Depth (height), grown as a spray-type: About 4.6 cm. Disc diameter: About 6 mm.

*Receptacles.*—Height: About 6 mm. Diameter: About 1.9 cm. Shape: Flattened globular. Color: Close to 145C.

*Inflorescence buds.*—Height: About 1.4 cm. Diameter: About 1.8 cm. Shape: Flattened globular. Texture and luster: Distally, smooth and glabrous; proximally, moderately pubescent; slightly glossy. Color: Close to 138A; immature ray florets, close to between 75C and 75D.

*Ray florets.*—Quantity and arrangement: About 400 arranged in about ten whorls. Length: About 3.8 cm, varying between 1.5 cm and 4.8 cm. Width: About 1.7 cm, varying between 0.6 cm and 2.1 cm. Shape: Oblanceolate; strongly concave and moderately carinate. Apex: Broadly and bluntly acute to shallowly emarginate. Base: Attenuate. Margin: Entire; not undulate. Aspect: Initially upright to about 45° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 75D strongly tinged with close to 150D; towards the apex, slightly tinged with close to 11A. When opening, lower surface: Close to between 150D and 155A; distally, tinged with close to 75D and at the apex, tinged with close to 11A. Fully opened, upper surface: Close to NN155A tinged with close to 75D and 56B; distally tinged with close to 155A; venation, similar to lamina colors; color does not change with development. Fully opened, lower surface: Close to NN155A; distally tinged with close to 155A; venation, similar to lamina colors; color does not change with development.

*Disc florets.*—Quantity and arrangement: About 30 massed at the center of the receptacle. Length: About 6 mm. Diameter: About 1 mm. Shape: Lower 80% fused into a tube; upper 20% free. Apex: Narrowly acute. Margin, free-part: Entire. Texture and luster, inner and outer surfaces: Smooth, glabrous; glossy. Color, when opening, inner and outer surfaces: Distally, close to 154D; at the apex, close to 150A; and proximally, close to 157A. Color, fully opened, inner and outer surfaces: Distally, close to between 150D and 154D; at the apex, close to 150A; proximally, close to 157A.

*Involucral bracts.*—Quantity and arrangement: About 34 arranged in about two whorls. Length: About 1.3 cm. Width: About 4 mm. Shape: Narrowly ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Close to 146B; margins, translucent and close to 192D and N199A. Color, lower surface: Close to 137B; margins, translucent and close to 192D and N199A.

*Peduncles.*—Length, terminal peduncle: About 6.8 cm. Diameter, terminal peduncle: About 5.5 mm. Length, third peduncle, when grown as a spray-type: About 11.8 cm. Diameter, third peduncle, when grown as a spray-type: About 3 mm. Strength: Strong. Aspect, terminal peduncle: Upright. Aspect, third peduncle, when grown as a spray-type: About 30° from the flowering stem axis. Texture and luster: Densely pubescent; moderately glossy. Color: Close to 138B; venation, close to 137B.

*Reproductive organs.*—Androecium: Present on disc florets only. Quantity: About five per floret. Filament length: About 2 mm. Filament color: Close to 145D. Anther size: About 0.5 mm by 1.5 mm. Anther shape: Narrowly oblong. Anther color: Close to 14A. Pollen amount: Moderate. Pollen color: Close to 17A. Gynoecium: Present on both ray and disc florets. Quantity: One per floret. Pistil length: About 1.1 cm. Style length: About 1 cm. Style color: Close to 150B to 150C. Stigma diameter: About 1 mm. Stigma shape: Cleft, decurrent. Stigma color: Close to 5A. Ovary color: Close to 145A.

*Seeds and fruits.*—To date, seed and fruit production have not been observed on plants of the new *Chrysanthemum.*

Pathogen & pest resistance: Plants of the new *Chrysanthemum* have been observed to be resistant to Fusarium Wilt (*Fusarium oxysporum* spp. *chrysanthemi* (FoNL1)). To date, plants of the new *Chrysanthemum* have not been observed to be resistant or tolerant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFEMPR11' as illustrated and described.

* * * * *